US009194942B2

(12) United States Patent
Gomersall

(10) Patent No.: US 9,194,942 B2
(45) Date of Patent: Nov. 24, 2015

(54) DERIVING IMAGE DATA FROM DATA RECEIVED FROM AN ULTRASOUND PROBE

(71) Applicant: William Henry Gomersall, Oxford (GB)

(72) Inventor: William Henry Gomersall, Oxford (GB)

( * ) Notice: Subject to any disclaimer, the term of this patent is extended or adjusted under 35 U.S.C. 154(b) by 116 days.

(21) Appl. No.: 14/215,217

(22) Filed: Mar. 17, 2014

(65) Prior Publication Data

US 2014/0286553 A1 Sep. 25, 2014

(30) Foreign Application Priority Data

Mar. 20, 2013 (GB) .................................. 1305190.9

(51) Int. Cl.
| | | |
|---|---|---|
| *G06K 9/00* | (2006.01) | |
| *G01S 7/52* | (2006.01) | |
| *G01S 15/89* | (2006.01) | |
| *A61B 8/00* | (2006.01) | |
| *A61B 8/08* | (2006.01) | |

(52) U.S. Cl.
CPC ......... *G01S 7/52047* (2013.01); *G01S 7/52082* (2013.01); *G01S 15/8915* (2013.01); *A61B 8/4427* (2013.01); *A61B 8/5207* (2013.01); *A61B 8/5223* (2013.01)

(58) Field of Classification Search
CPC .................................... G06K 9/00; A61B 8/00
USPC ......... 382/128, 129, 130, 131, 132, 133, 134; 600/407, 410, 411, 425, 427, 437
See application file for complete search history.

(56) References Cited

U.S. PATENT DOCUMENTS 5,339,815 A * 8/1994 Liu ........................ A22B 5/007
382/110

FOREIGN PATENT DOCUMENTS

EP 2085927 A1 8/2009

OTHER PUBLICATIONS

"Wavelet Restoration of Medical Pulse-Echo Ultrasound Images in an EM Framework", Ng et al, IEEE Transactions on Ultrasonics, Ferroelectrics, and Frequency Control, vol. 54, No. 3, Mar. 2007, pp. 550-568.

* cited by examiner

*Primary Examiner* — Abolfazl Tabatabai
(74) *Attorney, Agent, or Firm* — Richard M. Goldberg

(57) ABSTRACT

Apparatus for producing image data representing a specimen being imaged using ultrasound includes a processor and memory. The processor receives input data representing output from an ultrasound probe, and performs an iterative algorithm on the input data until a converged estimate of the mean of the distribution of the image data is reached. This estimate is used to produce output image data for display. The algorithm updates estimates for the image data, the echogenicity of the image data, and the variance of the noise of the image data. The step of updating the variance of the noise of the image data uses an update rule that assumes the noise to be varying across the image data but locally invariant for any small enough region of the image data.

20 Claims, 21 Drawing Sheets

$$\Sigma_n S^{-2} = \eta I \quad \text{—1401}$$

$$H^H \Sigma_n^{-1} \approx \Sigma_n^{-1} H^H \quad \text{—1402}$$

$$\mathbf{m}_k = (H^H \Sigma_{n,k}^{-1} H + S_k^{-2})^{-1} H^H \Sigma_{n,k}^{-1} \mathbf{y} \quad \text{—1403}$$

$$\Rightarrow \mathbf{m}_k = (H^H H + \Sigma_{n,k} S_k^{-2})^{-1} H^H \mathbf{y} \quad \text{—1404}$$

$$\mathbf{m}_0 \approx (H^H H + \eta I)^{-1} H^H \mathbf{y} \quad \text{—1405}$$

*Figure 14*

$$\underbrace{(H^H \Sigma_{n,k}^{-1} H + S_k^{-2})}_{A} \underbrace{\mathbf{m}_k}_{\mathbf{c}} = \underbrace{H^H \Sigma_{n,k}^{-1} \mathbf{y}}_{\mathbf{b}} \quad \sim 1801$$

$$A\mathbf{c} = \mathbf{b} \quad \sim 1802$$

$$AP^{-1}P\mathbf{c} = \mathbf{b} \quad \sim 1803$$

$$P^{-1} = (H^H H + \eta I)^{-1} \quad \sim 1804$$

*Figure 18*

DERIVING IMAGE DATA FROM DATA RECEIVED FROM AN ULTRASOUND PROBE

BACKGROUND OF THE INVENTION

1. Field of the Invention

The present invention relates to an apparatus and method for producing image data representing a specimen being imaged using ultrasound.

2. Description of the Related Art

Ultrasound machines produce an image of a specimen, usually an area below a patient's skin, by using a probe including one or more acoustic transducers to send pulses of sound into the specimen. The pulses are reflected back from materials within the specimen and the received signals are used to generate an image that can be displayed to an operator and/or stored.

However, the pulses generated by the transducers have a focal depth outside which the images become increasingly blurred. Thus, it is difficult to accurately image a specimen that has a large depth.

BRIEF SUMMARY OF THE INVENTION

According to an aspect of the present invention, there is provided apparatus for producing image data representing a specimen being imaged using ultrasound as set out in the claims.

According to another aspect of the present invention, there is provided a method of producing image data representing a specimen being imaged using ultrasound as set out in the claims.

BRIEF DESCRIPTION OF THE DRAWINGS

FIG. 14 shows equations used during the steps shown in FIG. 9 to obtain a first estimate of the image data;

FIG. 18 shows equations used during the steps shown in FIG. 17 to update an estimate of the image data;

DETAILED DESCRIPTION OF EXAMPLE EMBODIMENTS

FIG. 1

Figure 1:
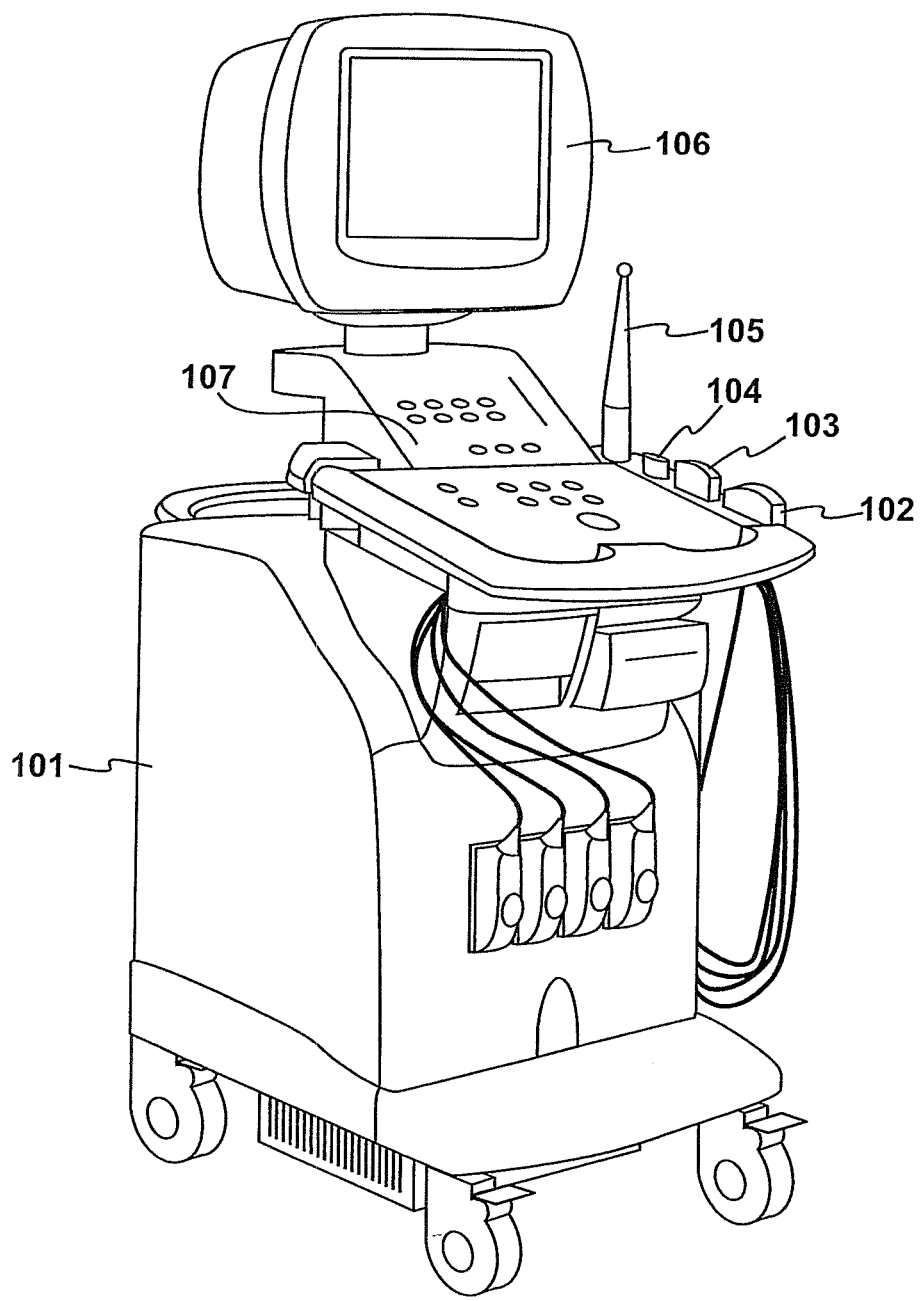
FIG. 1 shows an ultrasound machine suitable for use with the invention.

FIG. 1 illustrates a typical ultrasound machine. This includes a processing system 101 that receives input from a plurality of probes 102, 103, 104 and 105. A probe is held against a specimen to be imaged. Usually, this is the skin of a patient and the area immediately beneath the skin is imaged, but ultrasounds may also be taken of organs that have been removed from the body or of other materials.

A pulse is generated by the processing system 101 and sent to the probe in use, for example probe 102. This pulse is sent through the specimen and is reflected back. Data representing the reflections is returned to processing system 101 and displayed on display 106. An interface 107 is provided to allow an operative to control the machine.

Many alternative forms of ultrasound machine are available. In particular, portable machines that resemble laptops are often used, but these generally have less processing power and less memory, which can limit the quality of the displayed images.

FIG. 2

Figure 2:
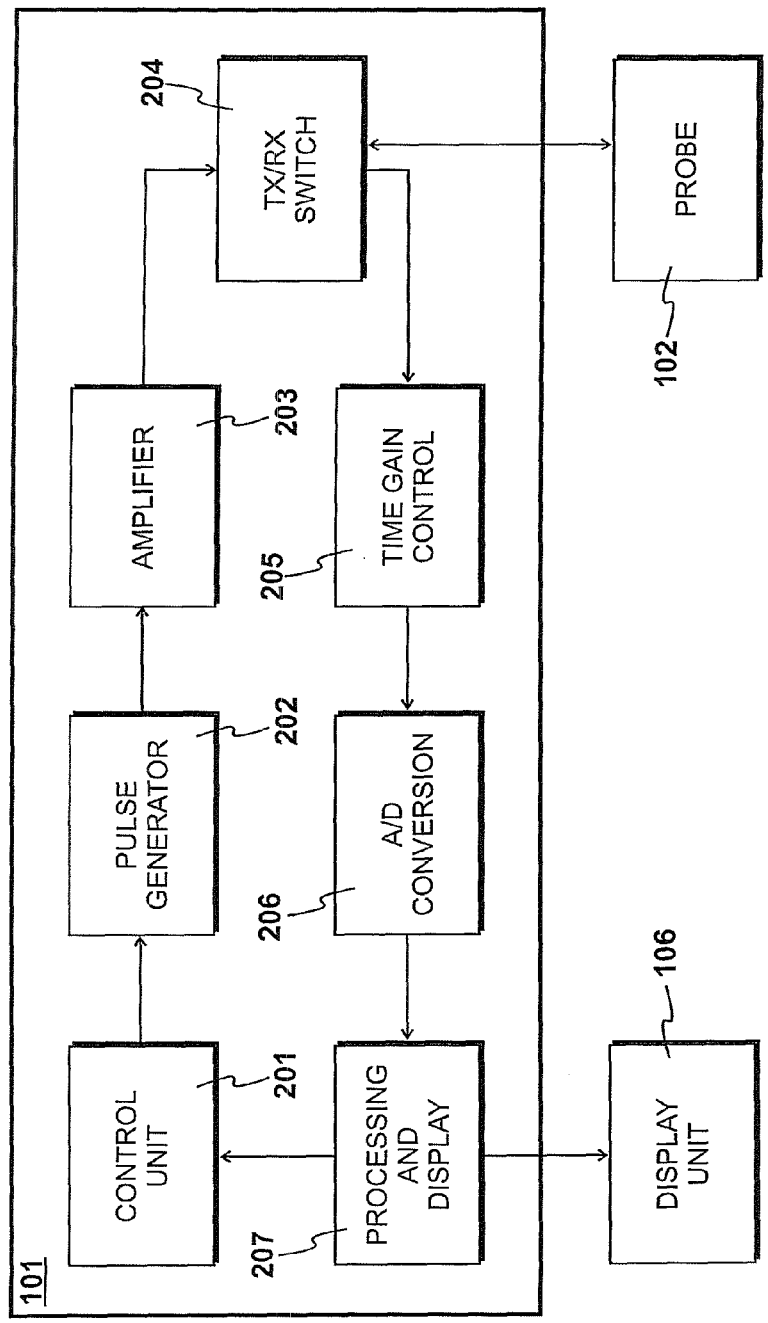
FIG. 2 shows components of the ultrasound machine shown in FIG. 1.

A block diagram of the processing system 101 shown in FIG. 1 is laid out in FIG. 2. A control unit 201 controls the overall process. It instructs pulse generator 202 to generate the appropriate pulse which is sent to amplifier 203 before being forwarded to a switch 204. The pulse is then sent to a probe, such as probe 102. When data is received back from the probe, this is sent via switch 204 to a time gain control unit 205. Analogue-to-digital conversion of the data is performed in unit 206 and a processing unit 207 converts the data into image data that is sent to display unit 106. Control unit 201 is then informed to start the process of generating a pulse again.

The processing system shown in FIG. 2 differs from traditional ultrasound processing systems, which generally perform envelope detection before the analogue-to-digital conversion, in that there are no non-linear steps before output is displayed. This reduces the amount of memory required.

Other processing systems that include a unit or units capable of carrying out the steps of the invention may also be used.

FIG. 3

Figure 3:
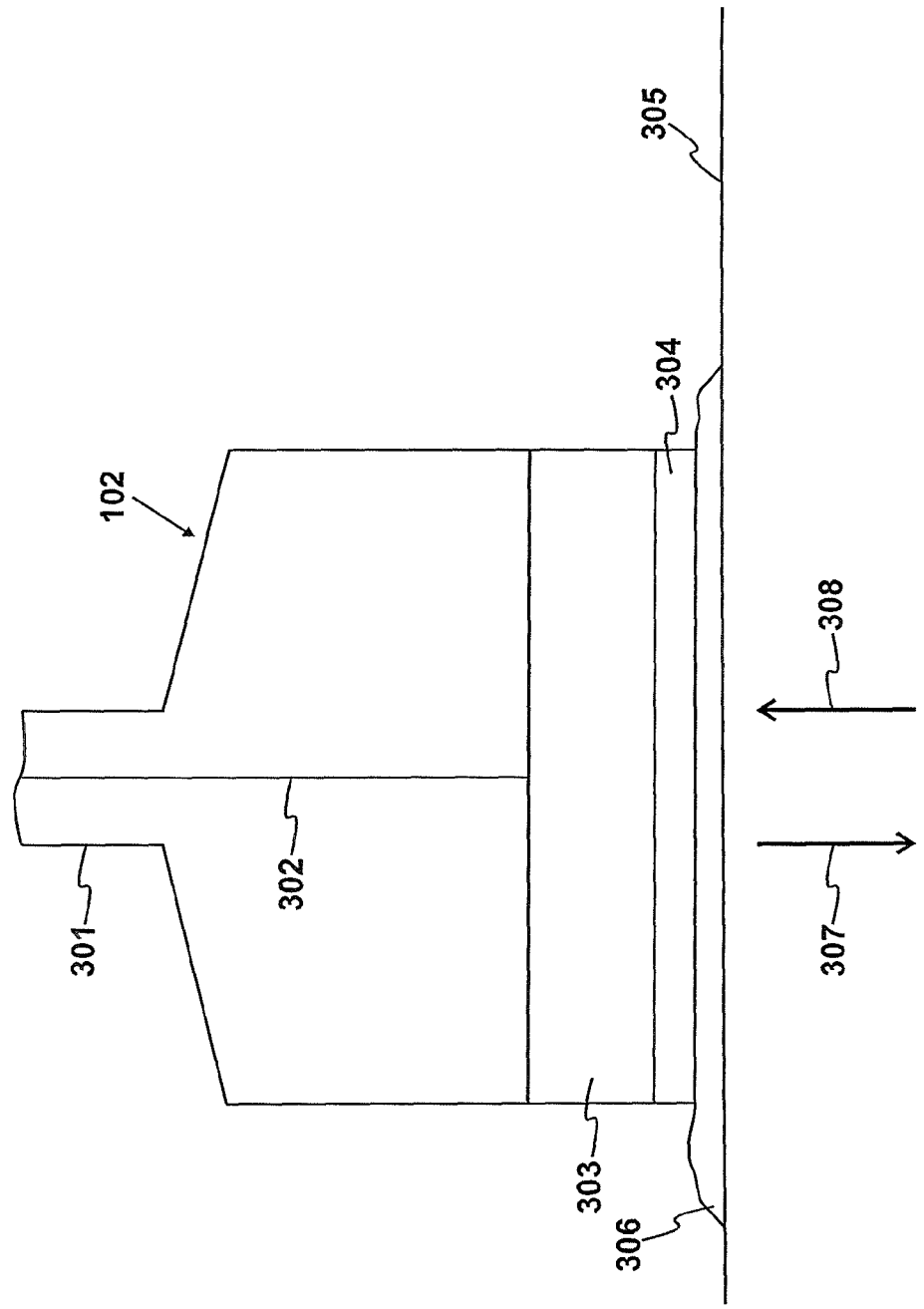
FIG. 3 illustrates a probe shown in FIG. 1.

Probe 102 is represented in FIG. 3. It is connected to processing system 101 by a cable 301 down which a control wire 302 is passed. This control wire sends signals to and receives signals from an array 303 of piezoelectric transducers.

A coating 304 forms the outer lower surface of probe 102. This can assist with impedance matching. The probe is placed against a patient's skin 305, usually with a layer of water-based gel 306 between the coating 304 and the skin 305.

When the probe receives signals from processing system 101, it produces sound waves using transducer array 303 as instructed, and these are passed into the patient's body as shown by arrow 307. Echoes 308 are received back to the transducers and are transmitted via wire 302 to processing system 101.

This happens several times a second and allows a picture of the area immediately below probe 102 in the patient's body to be built up and shown to the operator on display unit 106.

FIG. 4

Figure 4:
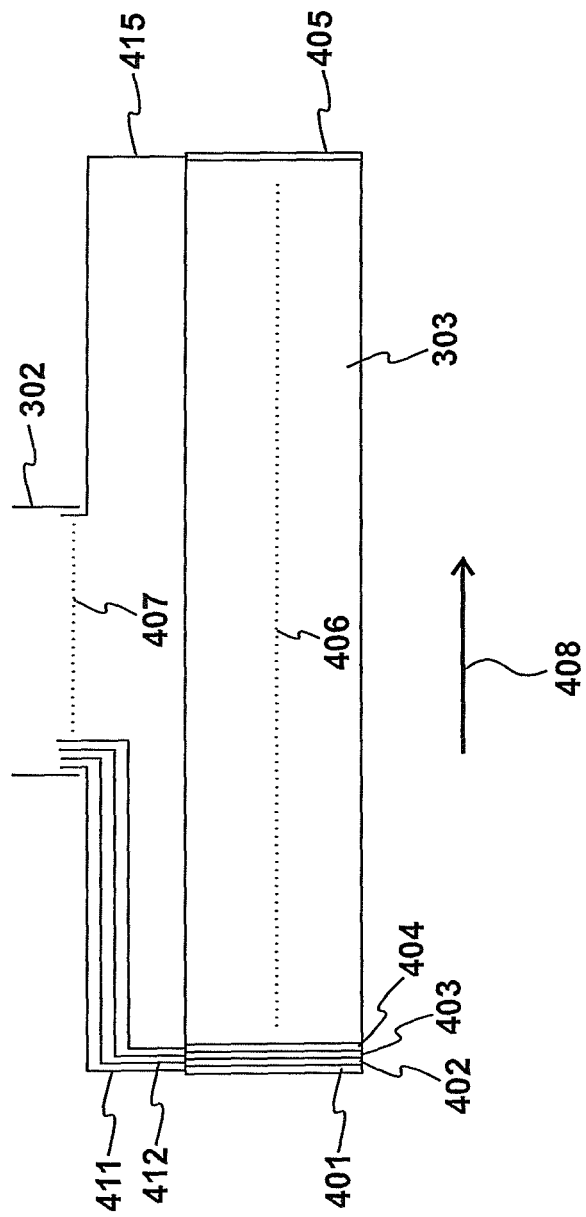
FIG. 4 illustrates an array of transducers shown in FIG. 3.

Transducer array 303 is shown in more detail in FIG. 4. It comprises a plurality of individual transducers, such as transducers 401, 402, 403, 404 and 405. Not all the transducers are shown in this figure for the purposes of clarity, as indicated by dotted line 406. In this example, probe 102 includes 128 individual transducers.

FIG. 4 also shows that wire 302 is actually made up of 128 separate wires, each controlling one transducer. Thus for example, transducer 401 is controlled by wire 411, transducer 402 is controlled by wire 412, transducer 405 is controlled by wire 415, and so on as indicated by dotted line 407. The instructions received from processing system 101 are simply instructions on a particular wire for the corresponding transducer to fire, and thus the probe does not include any processing capability of its own. The reflection received by each transducer is also sent along its own wire.

Typically, modern probes use transducer arrays such as that shown in FIG. 4 to produce focussed ultrasound beams. This allows a sweeping along the array in the lateral direction shown by arrow 408, thus producing a two-dimensional image by combining the reflections received from individual transducers. However, other types of probes may use transducers that are mechanically swept to create a focussed beam, or may use fewer or more transducers in their arrays, or may use two-dimensional arrays. The invention described herein can be used with any type of probe that forms focussed ultrasound beams, as long as the characteristics of the probe can be modelled.

FIG. 5

Figure 5:
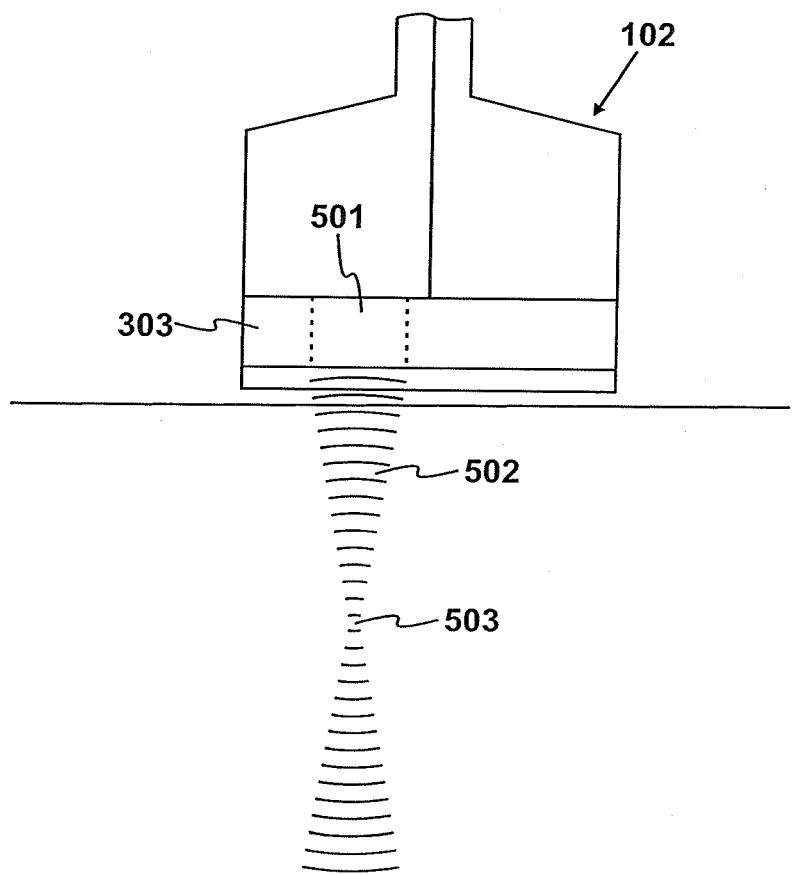
FIG. 5 illustrates a beam formed by a plurality of transducers shown in FIG. 4.

FIG. 5 illustrates how a subset of the transducers in array 303 are used to create a single ultrasound beam. In this example, a subset 501 comprises 32 adjacent individual transducers. These are excited in a particular order, which will be discussed further with reference to FIG. 6, in order to produce a focussed ultrasound beam 502. Typically, the left-most subset of transducers is fired first, and a step along, one transducer at a time, is made until the right-most set is fired. This creates a sweep in the direction of arrow 408.

As shown in FIG. 5, beam 502 is focussed at it narrowest point 503. This is where the image produced will be sharpest. Prior art methods of analysing the information received from probe 102 tend to produce blurring at other depths outside the focal area.

FIG. 6

Figure 6:
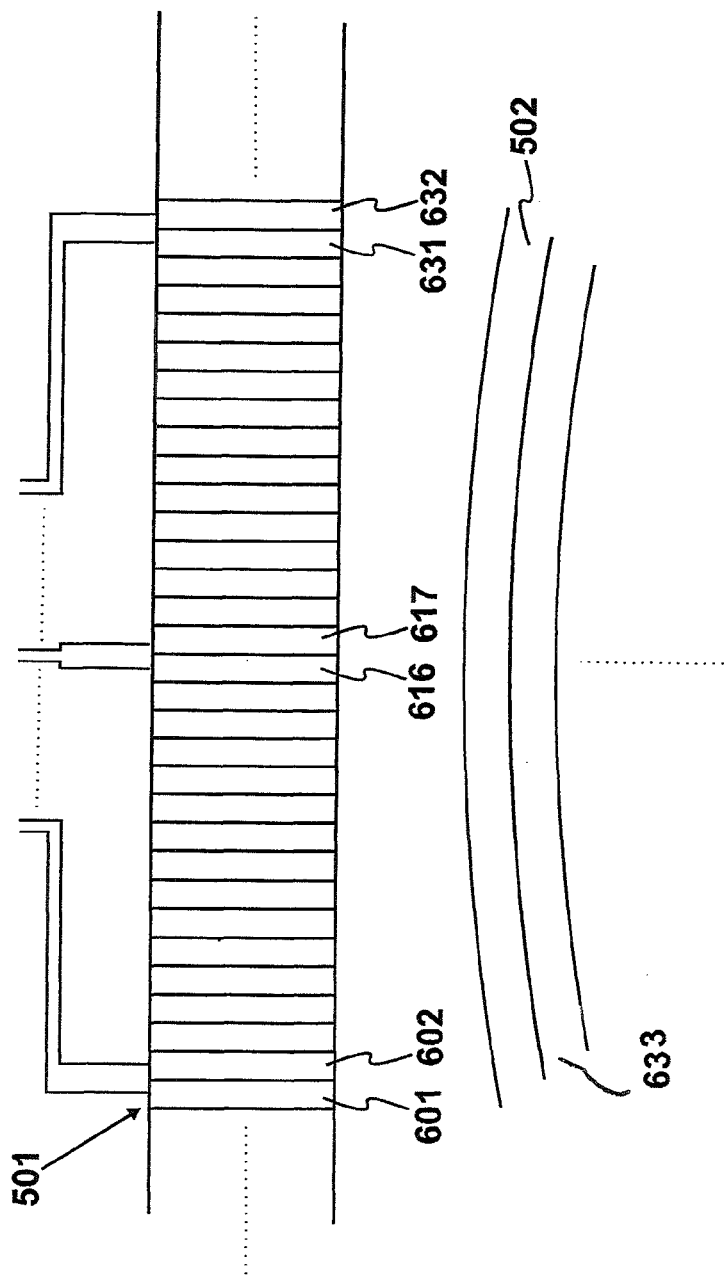
FIG. 6 illustrates how the plurality of transducers shown in FIG. 5 create the beam.

FIG. 6 illustrates how a subset 501 of transducers produces a single focussed beam 502.

The subset comprises, in this example, 32 transducers. Transducer 601 is the left-most transducer in the set, 602 is the next transducer and so on. Transducer 632 is the right-most transducer in the set with transducer 631 being adjacent to it. Transducers 616 and 617 are the central transducers.

In order to generate the beam 502 a wave front must be generated that will converge at the focus 503. This is achieved by first firing transducers 601, and 632, then transducers 602 and 631, and so on until finally transducer 616 is fired with transducer 617. This creates a wave front having the shape 633 shown in FIG. 6.

In prior art systems, the information returned by transducers 601 to 632 would have a delay and sum process applied to it in order to combine a single time trace for each step along array 303. This results in a small number of time traces that can be easily reproduced as image data and output to display 106. However, as previously described, the resulting image is only sharp at the depth represented by the focus 503, and is blurred everywhere else. The present invention provides a method of analysing the data received from all the transducers in array 303 having undergone a delay and sum process, to provide a less blurred image.

This invention has application for ultrasound probes having different arrangements of transducers, in addition to that illustrated herein.

FIG. 7

Figure 7:
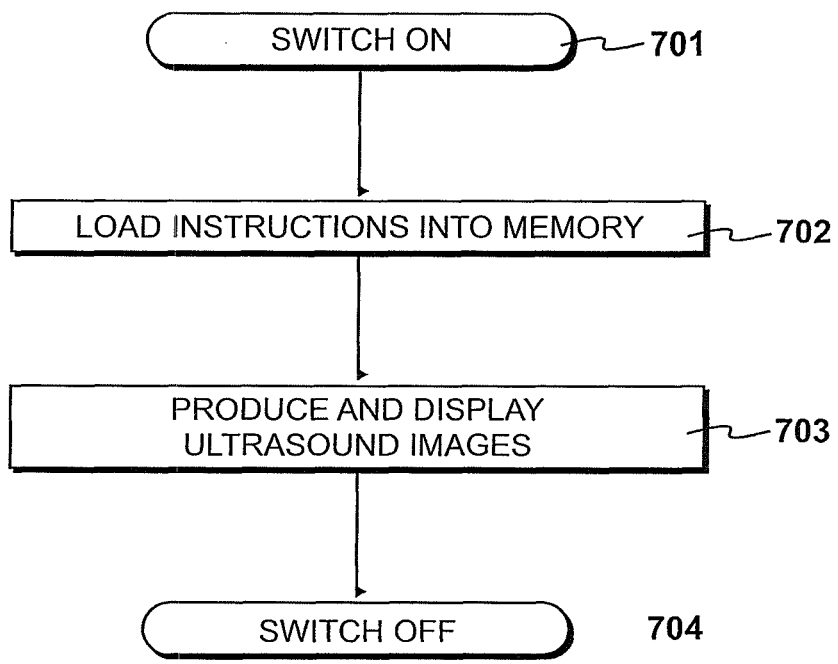
FIG. 7 details steps carried out by the ultrasound machine shown in FIG. 1.

Steps carried out by the ultrasound processing system 101 are described in FIG. 7. At step 701 the machine is switched on and at step 702 instructions are loaded into memory. These could be pre-installed instructions stored on a hard drive, instructions downloaded from a networked location, or instructions installed from a local removable drive, such as a CD-ROM or flash drive.

At step 703 ultrasound images are produced and displayed, and at step 704 the machine is switched off.

FIG. 8

Figure 8:
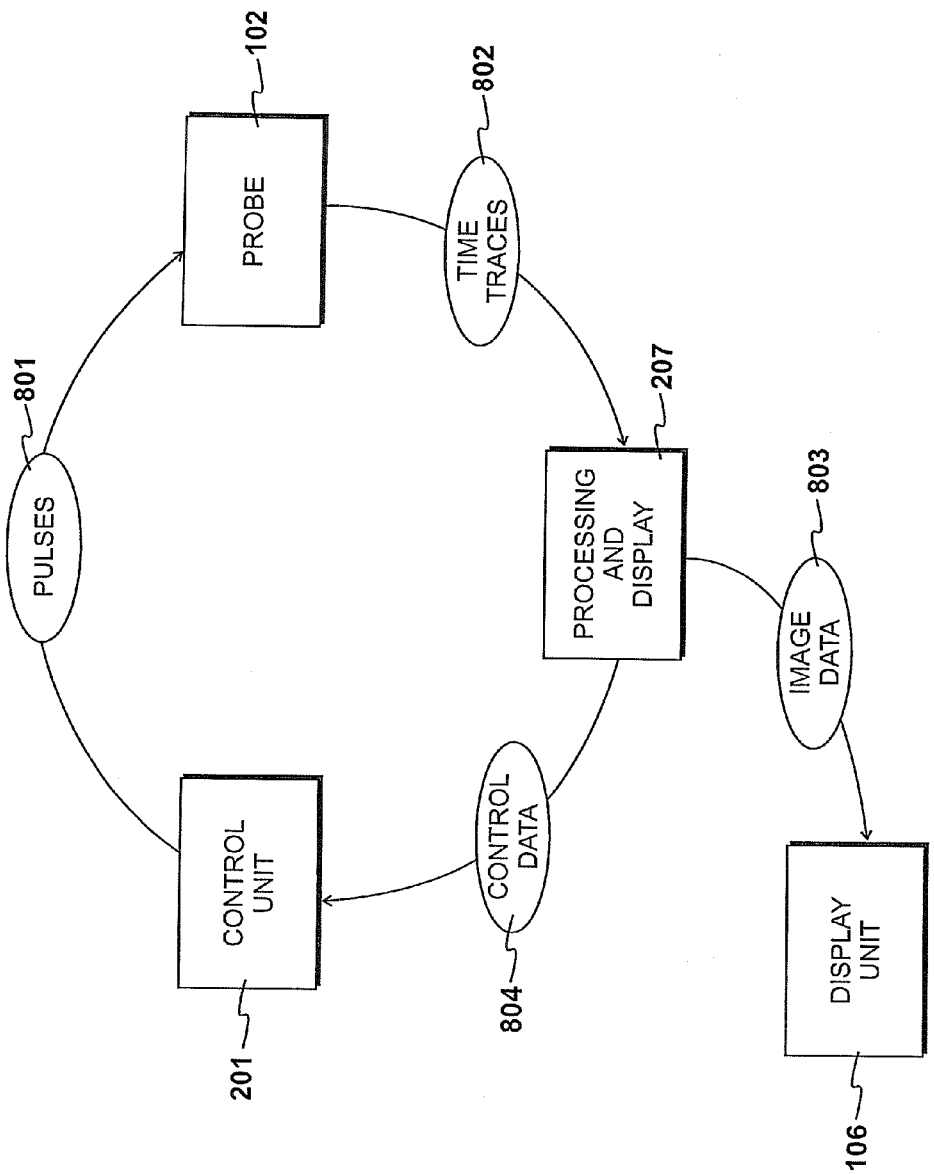
FIG. 8 is a diagram of the process of producing image data by the ultrasound machine shown in FIG. 1.

Operation of the ultrasound machine shown in FIG. 1 is illustrated diagrammatically in FIG. 8. The control unit 201 sends pulses 801 to the probe 102. The probe returns data which is supplied as time traces 802 to processing unit 207. Unit 207 supplies image data 803 to display 106 and control data 804 to control unit 201, indicating that the cycle may begin again. It will be appreciated that this is a greatly simplified description of the operation of the machine shown in FIG. 1. This description will not go into detail regarding the control unit 201, the generation of pulses or the receiving of information from the probe. Nor will the beam-forming techniques used to create a beam such as beam 503 be further discussed. The invention herein described relates to the processing of the time traces 802 and conversion of them into image data 803 by processing unit 207. This can be done with any method of producing the time traces, by any suitable ultrasound machine and probe.

FIG. 9

Figure 9:
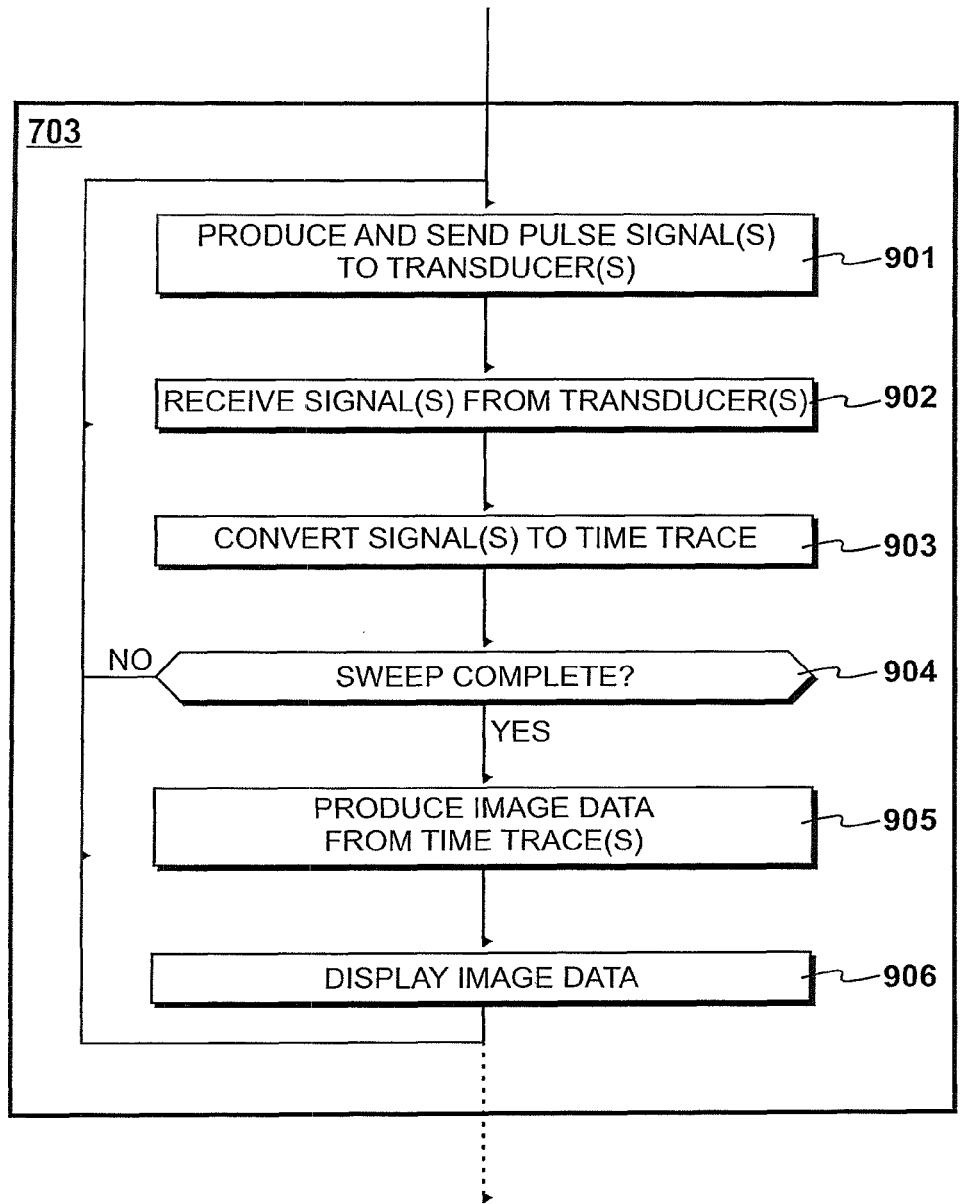
FIG. 9 details steps carried out during FIG. 7 to produce image data.

FIG. 9 details step 703 at which ultrasound images are produced and displayed. At step 901 at least one pulse signal is produced and sent to at least one transducer, and at step 902 answering signals are received. At step 903 these signals are converted to time traces and at step 904 a question is asked as to whether the sweep of array 303 is complete. If this question is answered in the negative, control is returned to step 901 and more pulses are generated.

However, if the sweep is complete then at step 905 image data is produced from the time traces by processing unit 207 and at step 906 it is displayed to the operator on display 106.

Control is then returned to step 901. However, at any time an interrupt may be received indicating that the machine is to be switched off, leading to a completion of step 703.

The remainder of this description will concentrate on further detailing step 905.

FIG. 10

Figure 10:
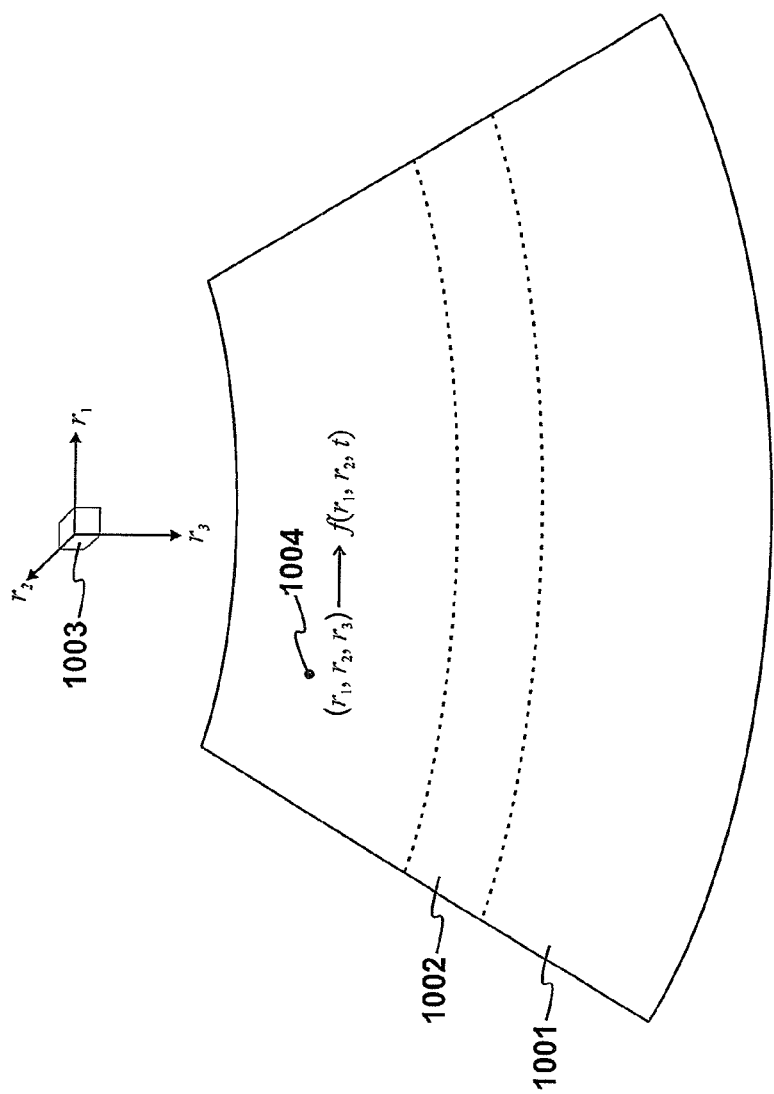
FIG. 10 illustrates the space being imaged.

FIG. 10 illustrates the image data being produced by the ultrasound machine shown in FIG. 1. It includes an area 1001 corresponding to the area of the patient being imaged. The top of the picture represents the area closest to the probe 102.

Area 1002, marked with dotted lines, represents the area in which a traditional ultrasound image would be focussed. The remainder of the image, constituting most of the image space 1001, would be blurred to a greater or lesser degree. The invention herein described aims to improve upon traditional ultrasound by providing a less blurred image throughout.

Figure 11:
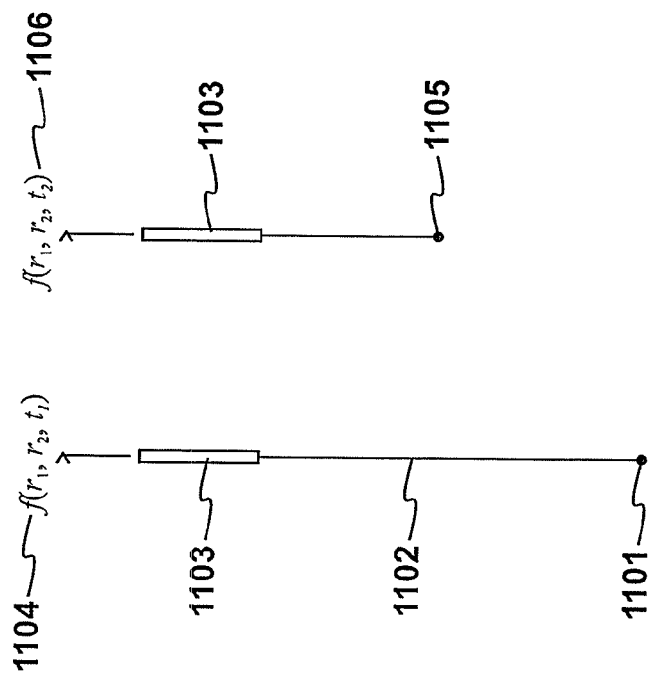
FIG. 11 is a diagram of a pulse being reflected from a scatterer.

Axes 1003 illustrate the reference frame of the area being imaged: $r_1$ represents the lateral direction, or the direction along transducer array 303. Direction $r_2$ represents the elevation direction and direction $r_3$ is the depth into the specimen. Any point, such as point 1004, in space 1001 can therefore be represented as a three-dimensional point ($r_1$, $r_2$, $r_3$). When an ultrasound beam from a transducer is reflected from it, this generates a time trace, which is some function of $r_1$, $r_2$ and t, where t is the time taken to receive an echo at the transducer.
FIG. 11

Figure 12:
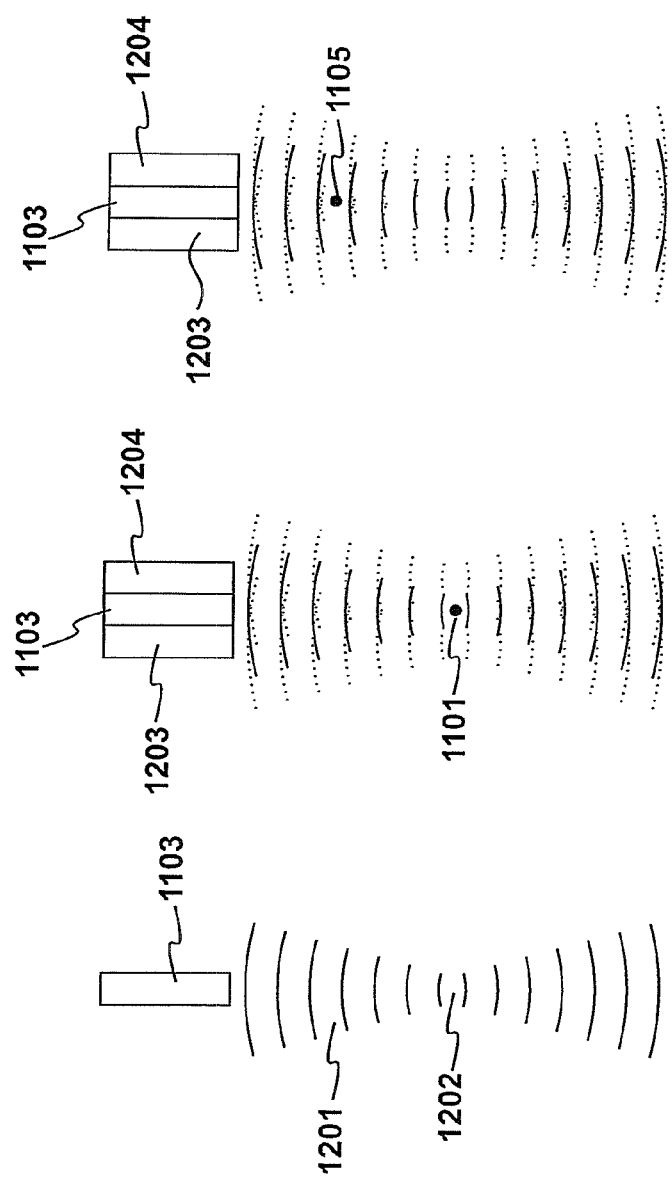
FIG. 12 is a diagram of a plurality of pulses being reflected from a scatterer.

FIG. 11 is a representation of how the reflection of a point in space is converted to a time trace by a transducer. The point 1101 reflects an ultrasound pulse 1102 generated by transducer 1103. This results in a time trace 1104 which has co-ordinates $r_1$ and $r_2$ in the lateral and elevational directions respectively, and a first time measurement $t_1$, representing the amount of time it took for the pulse to be reflected. A point 1105 which is on the same line as point 1101 but at a smaller depth, would have the same lateral and elevational entries in its time trace 1106, but a smaller time measurement $t_2$. In a perfect world, it would therefore be a simple matter to equate time with depth and display the time traces to an operator accordingly. However, a pulse is not a neat line, but a wave having a focal point. In reality, each scatterer is reflected back to more than one transducer.
FIG. 12

FIG. 12 is a more real-world illustration of what happens when a pulse is reflected back from a scatterer. Transducer 1103 produces a pulse 1201 that has a waveform having a focus at point 1202. When a plurality of transducers are placed side-by-side, each produces a pulse that interferes with its neighbours' waveforms.

The pulses of transducers 1203 and 1204, which are adjacent to transducer 1103, are also shown in dotted lines. The delay and sum technique commonly used by ultrasound probes takes advantage of the Huygens principle, whereby each transducer's pulses are considered as an individual source that contribute to an overall wave front. As illustrated in the Figure, the beams produced by transducers 1203, 1103 and 1204 therefore contribute to an overall wave front having a focal point defined where the waves sum coherently. Thus, waves reflected by a scatterer located at point 1101 will also be coherent, and when each transducer's time trace is displayed, the image of the scatterer will appear sharp.

However, point 1105 is closer to the transducers and so is outside the focal area. The time trace produced by each transducer is therefore slightly different in both the lateral and the time directions, as reflections from a scatterer at point 1105 are not coherent. Thus, a simple reproduction of the time traces as image data will lead to a blurring at point 1202, i.e. it will look larger than it should be.

Figure 13:
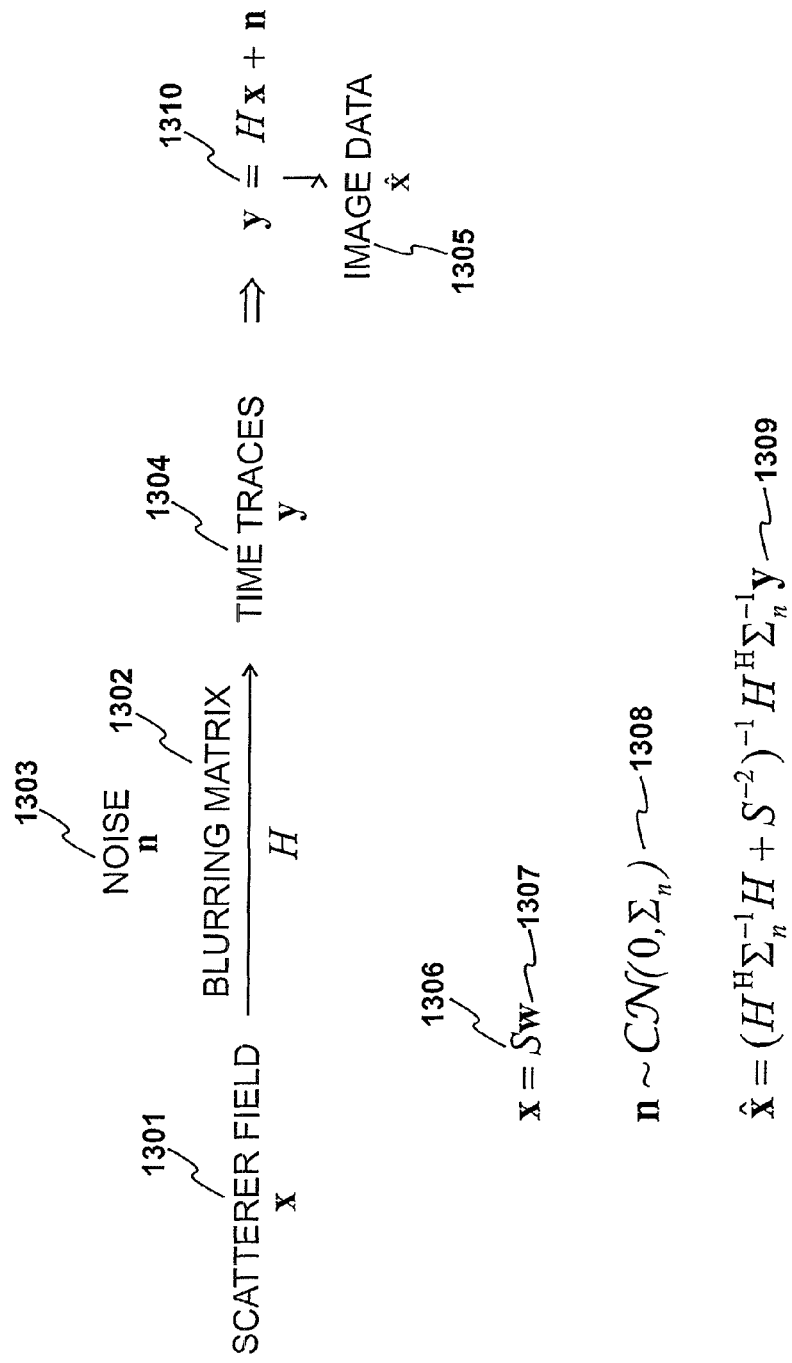
FIG. 13 shows equations used during the steps shown in FIG. 9 to obtain the image data.

When this effect is taken into account for the many scatterers that are present in a specimen being imaged, then it will be understood that if many scatterers are enlarged through blurring then they will start to merge together, and a loss of sharpness outside the focus depth is the result.
FIG. 13

The described invention therefore proposes a different way of dealing with the time traces, rather than traditional delay and sum post-processing techniques which fail to take account of the blurring.

For any given probe and for a type of specimen being imaged, it is possible to construct a blurring matrix which encapsulates how a scatterer at each point in the space being imaged will be reflected back to the transducers in the array. This is a function of a number of parameters, such as the way in which the transducers are fired, the speed of sound through the specimen being imaged, and so on. Thus, for each probe and type of specimen, a blurring matrix can be calculated or retrieved from memory as necessary. Thus the ultrasound process can be represented as shown in FIG. 13.

The field of scatterers can be modelled as a vector 1301, x. This is passed through a blurring matrix 1302, H, and is also subject to noise 1303, n, to produce time traces 1304, y. This leads to equation 1310, that y is equal to the sum of the product of H and x, and n:

$$y=Hx+n$$

Given that y is known, H is known and n can be modelled, we can arrive at an estimate for x. This estimate is what is displayed on display 106 as image data, and is as close as possible to the original scatterer field.

However, estimating x is not simple because H is very large and is not invertible. Typically H, a non-sparse matrix, might have 1,000,000 rows and columns. Thus, obtaining x using a simple multiplication by the inverse of H is not possible. Further, any calculation using H will be slow and may not fit in the memory of the processing unit.

Thus the problem is to estimate x given y and H. In order to do this, x is modelled as a product of its echogenicity 1306, S, and a random noise-like component 1307, w:

$$x=Sw$$

S is a diagonal matrix of real valued, non-negative echogenicity values and w is a random vector of complex valued zero mean Gaussian values. S is the same size as H and w is the same size as x. However, because S is diagonal it is easier to use than H.

The noise 1303 is assumed to have a circularly symmetric complex Gaussian distribution with zero mean and co-variance $\Sigma_n$, as shown in equation 1308:

$$n \sim CN(0, \Sigma_n)$$

Given this, the estimation of x can be configured as inferring the distribution of x conditioned on the data y, but with consideration to the parameters S and $\Sigma_n$. This can be done by iterating between finding the distribution of x and improving point estimates of S and $\Sigma_n$. The best estimate 1309 of x can be written as follows:

$$\hat{x}=(H^H\Sigma_n^{-1}H+S^{-2})^{-1}H^H\Sigma_n^{-1}y$$

This is the maximum a posteriori estimate for x, which is equivalent to the mean of the conditional distribution on x.
FIG. 14

By making certain assumptions about the underlying scatterer field, equation 1309 can be simplified and made more calculable.

First, the nature of the noise 1303 is considered. Noise may come from a variety of sources. For example, white noise is introduced at the amplifier stage, cross channel coupling between transducer wires can occur, and so on. Because so much of the noise is electrical, prior art systems generally assume that the noise is invariant across the scatterer field, i.e. the time trace from each transducer includes the same amount of noise.

However, noise is also due to other factors. Non-linear effects can be caused by pulses being reflected off more than one scatterer, or probe interface reverberation. Noise may also be caused by reflection to a scatter in the side lobes on an ultrasound beam or simply an incorrect calculation of the blurring matrix 1302. Consideration of this type of noise gives rise to the understanding that the noise field varies across the scatterer field, and may in fact be scaled across the image dependent upon the scatterer field.

Thus an assumption can be made that the co-variance $\Sigma_n$ of the noise is in proportion to the co-variance $S^2$ of the non-conditional distribution of x. This can be written as equation 1401, that the product of $\Sigma_n$ and the inverse of $S^2$ is some constant q multiplied by the identity matrix:

$$\Sigma_n S^{-2} \eta I$$

A value of 0.3 for $\eta$ has been found to be effective.

While the assumption is made that the noise variance varies with the signal variance, another assumption can be made that the noise variance varies slowly, such that it can reasonably be assumed to be constant across the support of the point spread function. This leads to the approximation that the product of the Hermitian transpose of H and the inverse of $\Sigma_n$ is approximately equal to the product of the inverse of $\Sigma_n$ and the Hermitian transpose of H, as shown at 1402:

$$H^H \Sigma_n^{-1} \approx \Sigma_n^{-1} H^H$$

As described with respect to FIG. 13, a technique for finding an estimate of the image data x is to iterate to a solution of the mean of the conditional distribution on x; the kth iteration of this is written as $m_k$. The kth estimate $m_k$, following equation 1309, is therefore the product of the following: the inverse of the sum of the product of the Hermitian transpose of H, the inverse of the kth iteration of $\Sigma_n$ and H, and the kth iteration of the inverse of $S^2$; the Hermitian transpose of H; the kth iteration of the inverse of $\Sigma_n$; and y, as shown at 1403:

$$m_k = (H^H \Sigma_{n,k}^{-1} H + S_k^{-2})^{-1} H^H \Sigma_{n,k}^{-1} y$$

Substituting in approximation 1402 gives the simplified estimate $m_k$ to be equal to the product of the following: the inverse of the product of the Hermitian transpose of H and H, added to the product of the kth iteration of $\Sigma_n$ and the kth iteration of the inverse of $S^2$; the Hermitian transpose of H; and y, as shown at 1404:

$$m_k = (H^H H + \Sigma_{n,k} S_k^{-2})^{-1} H^H y$$

Using assumption 1401, an initial estimate for m can therefore be written as the product of the following: the inverse of the product of the Hermitian transpose of H and H, added to the product of $\eta$ and the identity matrix; the Hermitian transpose of H; and y, as shown at 1405:

$$m_0 = (H^H H + \eta I)^{-1} H^H y$$

Thus an initial approximation $m_0$ can be made that is dependent only upon the blurring matrix 1302, H, and the time traces 1304, y. This is still a very large calculation, but, as will be shown in FIG. 15, if it is considered in the appropriate domain it becomes tractable.

FIG. 15

As previously discussed, both $\Sigma_n$ and S are diagonal matrices, and thus, although large, are sparse and can fit in memory. However, the blurring matrix H is very large and full, and calculations with it require a large amount of memory and time.

So far only the lateral time domain 1501 has been considered, which has axis in the lateral $r_1$ direction, the elevation $r_2$ direction and time. A Fourier transform 1502 in the $r_1$ and $r_2$ directions transforms domain 1501 into the lateral K-time domain 1503, where the lateral direction is transformed into the K-lateral direction and the elevation direction into the K-elevation direction respectively. Because the blurring matrix 1302, H, is invariant across the lateral direction in domain 1501, applying Fourier transform 1502 to it gives a block diagonal matrix 1504. A similar effect occurs with the elevational direction. Matrix 1504 is made up of a plurality of sub-matrices, such as matrices 1508, 1509, and so on. Each of these sub-matrices is small and can therefore fit into the memory of a typical processing system.

Thus, in order to calculate, for example, matrix 1505, which is the first part of equation 1405, a plurality of sub-matrices 1506 can be calculated and combined into a single matrix, the inverse Fourier transform of which is the required matrix. In other words, in order to calculate the inverse of the sum of the product of the Hermitian transpose of H and H and the identity matrix scaled by $\eta$:

$$(H^H H + \eta I)^{-1}$$

the Fourier transform 1502 is applied to the matrix H to produce a plurality of sub-matrices $H_{sub,i}$, where i indicates the ith sub-matrix. Because $\eta I$ is a diagonal constant matrix, it passes unchanged through the Fourier transform 1502. Thus, for each value of i, the inverse of the sum of the product of the Hermitian transpose of $H_{sub,i}$ and $H_{sub,i}$, and the appropriate sub-matrix of the identity matrix scaled by $\eta$, can be calculated:

$$(H_{sub,i}^H H_{sub,i} + \eta I_{sub,i})^{-1}$$

The resultant sub-matrices are combined into a single matrix and transformed back to the lateral time domain 1501 using inverse Fourier transform 1507 to give a result for matrix 1505.

Other calculations involving the blurring matrix H can be similarly carried out in domain 1503. However, because $\Sigma_n$ and S are diagonal in the lateral time domain, calculations involving these matrices are carried out in domain 1501.

FIG. 16

Figure 16:
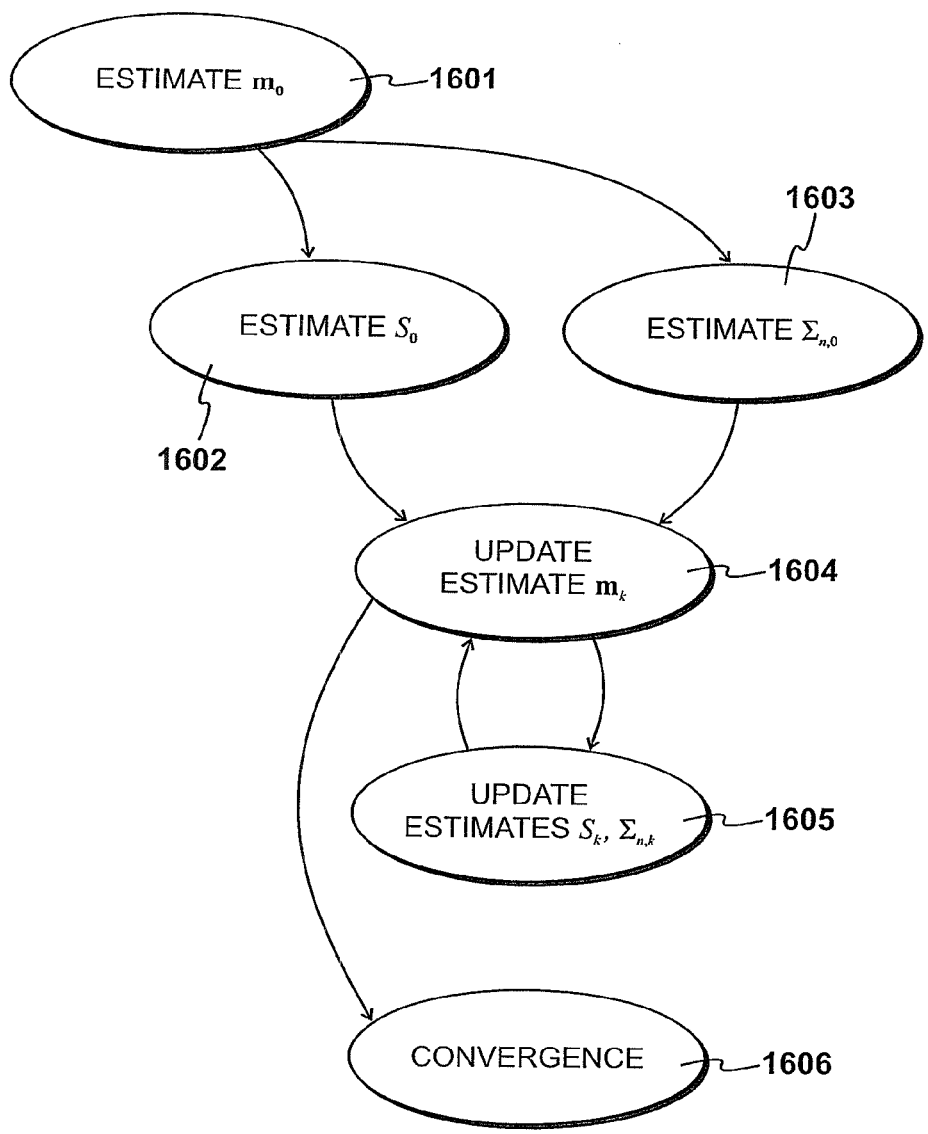
FIG. 16 is a diagram of the algorithm used to obtain the image data.

The procedure for estimating the scatterer field x is shown diagrammatically in FIG. 16.

Figure 20:
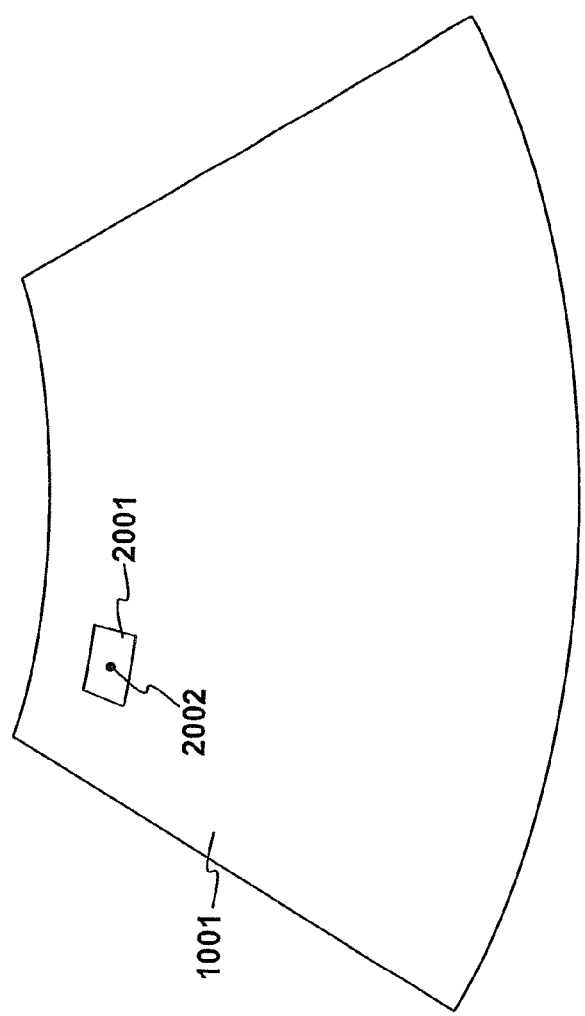
FIG. 20 shows equations used during the steps shown in FIG. 17 to update the estimate of the covariance of the noise of the image data.

A first estimate 1601 is made of the distribution of the image data. This estimate is used to make a first estimate 1602 of the echogenicity, $S_0$, and a first estimate 1603 of the co-variance of the noise, $\Sigma_{n,0}$. The method of obtaining these last two estimates will be described further with reference to FIGS. 20 to 22.

The first estimates of the echogenicity and of the variance of the noise are then used to update the estimate of the mean of the distribution of the image data at 1604. This estimate is then used to update the estimates for the echogenicity and the co-variance of the noise at 1605. The process then iterates between step 1604 and step 1605 until a satisfactory convergence is reached at 1606. The threshold for convergence can be defined as necessary. However, around six iterations of steps 1604 and 1605 are generally required to reach a satisfactory convergence. This algorithm is a form of the Expectation Maximisation algorithm.

Figure 15:
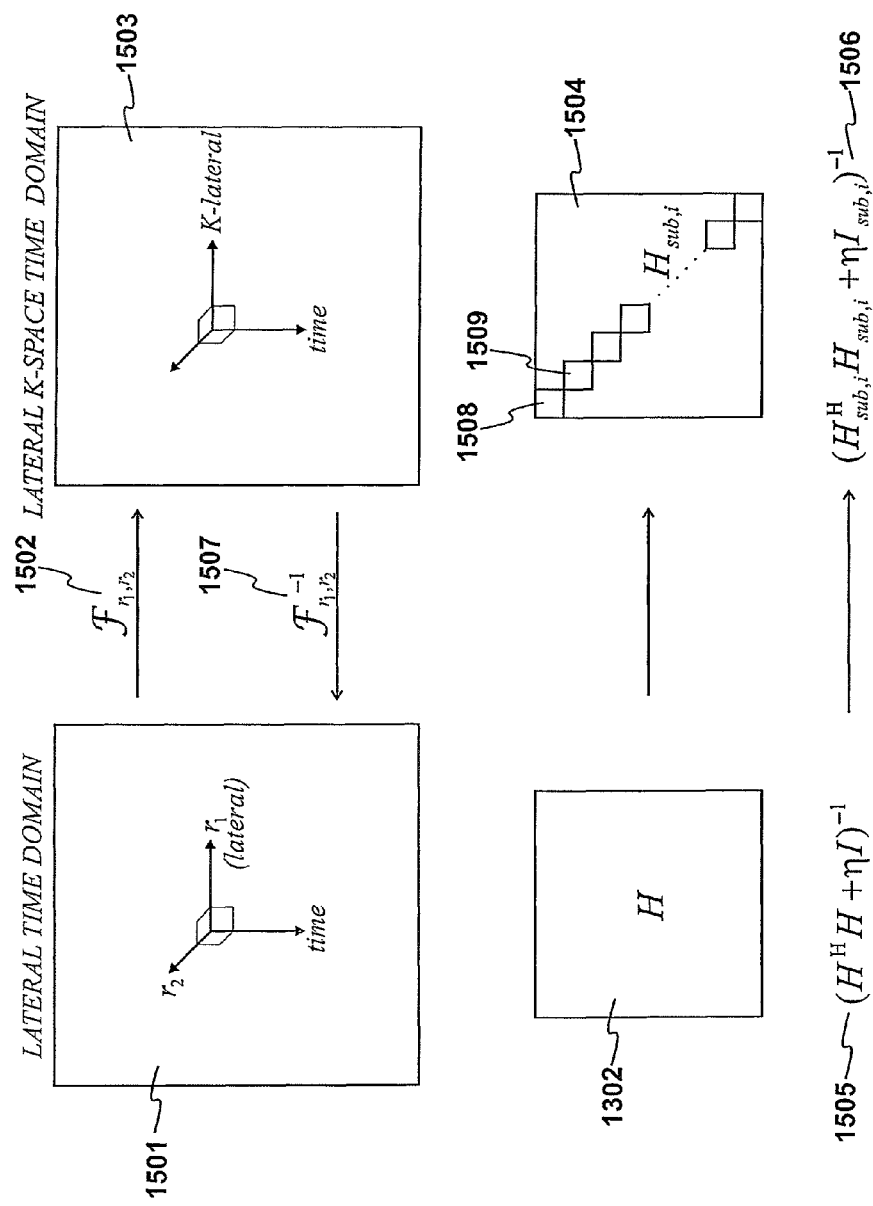
FIG. 15 illustrates a transformation into a different domain to calculate a matrix shown in FIG. 14.

The first estimate of the mean of the distribution of the image data $m_0$ found at 1601, is calculated using equation 1405. This involves calculating matrix 1505 as shown in FIG. 15. This matrix is stored for later use as it is used in the step of updating the estimates $m_k$, using equation 1403, at step 1604.

In an alternative embodiment, first estimates of the echogenicity and the co-variance of the noise can be obtained first and used in step 1604 to obtain a first estimate of $m_k$.

In this description, the input data into the above procedure is the time traces, y, and the ultimate result will be dependent upon this input data. However, it is possible that the procedure could be used to de-blur other, similar, data, and thus the input data is not limited to time traces.

FIG. 17

Figure 17:
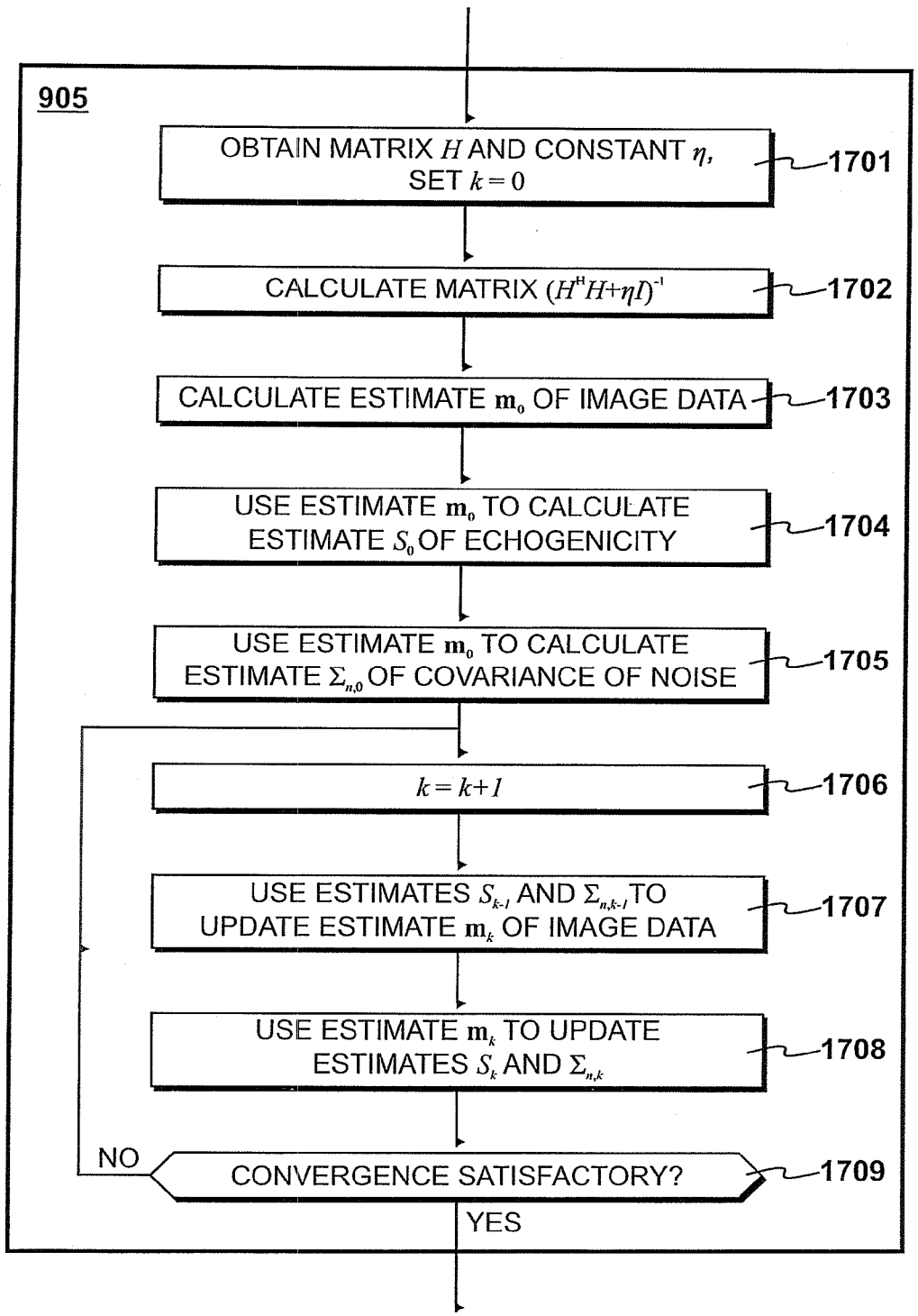
FIG. 17 details steps carried out during FIG. 9 to carry out the algorithm shown in FIG. 16.

FIG. 17 details step 905 carried out by processing system 101 to produce image data from the input time traces. This uses the process outlined in FIG. 16.

First at step 1701 an appropriate blurring matrix H and constant q are retrieved from memory. The variable k is set to zero. At step 1702 the matrix 1505 is calculated, and at step 1703 this matrix, H and the input time traces are used in equation 1405 to generate the first estimate $m_0$ of the image data.

At step 1704 the estimate $m_0$ is used to calculate the first estimate $S_0$ of the echogenicity, using any appropriate method. At step 1705 it is used to calculate the first estimate $\Sigma_{n,0}$ of the co-variance of the noise, as will be further described with reference to FIG. 20.

At step 1706 k is incremented by one and, at step 1707, what are now estimates $S_{k-1}$ and $E_{n,k-1}$ are used to update the estimate $m_k$ of the image data using equation 1404, At step 1708 this new estimate $m_k$ is used to update the estimate $S_k$ of the echogenicity and $\Sigma_{n,k}$ of the covariance of the noise. At 1709 a question is asked as to whether the convergence of the process is satisfactory. If this question is answered in the negative then control is returned to step 1706, k is incremented by one and steps 1707 and 1708 are carried out again. If, however, the convergence is satisfactory then step 905 is completed. The last estimate $m_k$ of the mean of the distribution of the scatterer field, is used as the best estimate of the scatterer field, and is therefore output as image data to be displayed on display unit 106. The methods of performing the calculations of $m_k$, $S_k$ and $\Sigma_{n,k}$ at steps 1707 and 1708 will now be detailed with respect to FIGS. 17 to 21.

At step 1706 k is incremented by one and, at step 1707, what are now estimates $S_{k-1}$ and $\Sigma_{n,k-1}$ are used to update the estimate $m_k$ of the image data using equation 1404, At step 1708 this new estimate $m_k$ is used to update the estimate $S_k$ of the echogenicity and $\Sigma_{n,k}$ of the covariance of the noise. At 1709 a question is asked as to whether the convergence of the process is satisfactory. If this question is answered in the negative then control is returned to step 1706, k is incremented by one and steps 1707 and 1708 are carried out again. If, however, the convergence is satisfactory then step 905 is completed. The last estimate $m_k$ of the mean of the distribution of the scatterer field, is used as the best estimate of the scatterer field, and is therefore output as image data to be displayed on display unit 106. The methods of performing the calculations of $m_k$, $S_k$ and $\Sigma_{n,k}$ at steps 1707 and 1708 will now be detailed with respect to FIGS. 17 to 22.

FIG. 18

As described with reference to FIG. 15, the initial estimate of the image data $m_0$ can be calculated in the lateral K-space time domain 1503, because it includes only the blurring matrix H, which is diagonalised by the Fourier transform, and a constant. Matrix 1403, which includes the terms $\Sigma_n$ and S, cannot be calculated in this way, because $\Sigma_n$ and S, while diagonal in the lateral time domain 1501, become non-diagonal and full in the lateral K-space time domain 1503. Thus, a different method must be used to calculate $m_k$.

The Conjugate Gradients algorithm is used at each iteration of step 1707. Equation 1403 can be rewritten as equation 1801, as follows:

$$\underbrace{\left(H^H \sum_{n,k}^{-1} H + S_k^{-2}\right)}_{A} \underbrace{m_k}_{c} = \underbrace{H^H \sum_{n,k}^{-1} y}_{b}$$

which is of the form Ac=b, as shown at 1802. The Conjugate Gradients algorithm solves this type of equation by finding the value of c that minimises the least squares difference. It is guaranteed to converge in the same number of iterations as the dimension of the matrix A. However, in our case the matrix A may have dimensions of order 1,000,000 by 1,000,000 entries, which makes for very slow convergence.

The algorithm can be speeded up by use of a preconditioner P. The equation to be solved is rewritten as $A\ P^{-1}Pc=b$, as shown at 1803. If $P^{-1}$ is cheap to compute, the Conjugate Gradients algorithm can then be used to solve for Pc, from which c can be found. The idea of preconditioning is to produce the matrix $AP^{-1}$ that is more amenable to fast inversion than A on its own, meaning that the algorithm converges in fewer iterations. A good preconditioner is an approximation to $A^{-1}$ that is cheaply invertible.

In the case under consideration, the matrix $A^{-1}$ is the first part of equation 1403, which as discussed with reference to FIGS. 14 and 15 can be approximated by matrix 1505. At this stage of the process, this matrix has already been calculated in order to provide the first estimate of the image data. Not only is it a close approximation of the required matrix, but it is relatively easy to invert. Thus it can be used as the preconditioner in the Conjugate Gradients algorithm, as shown at 1804.

FIG. 19

Figure 19:
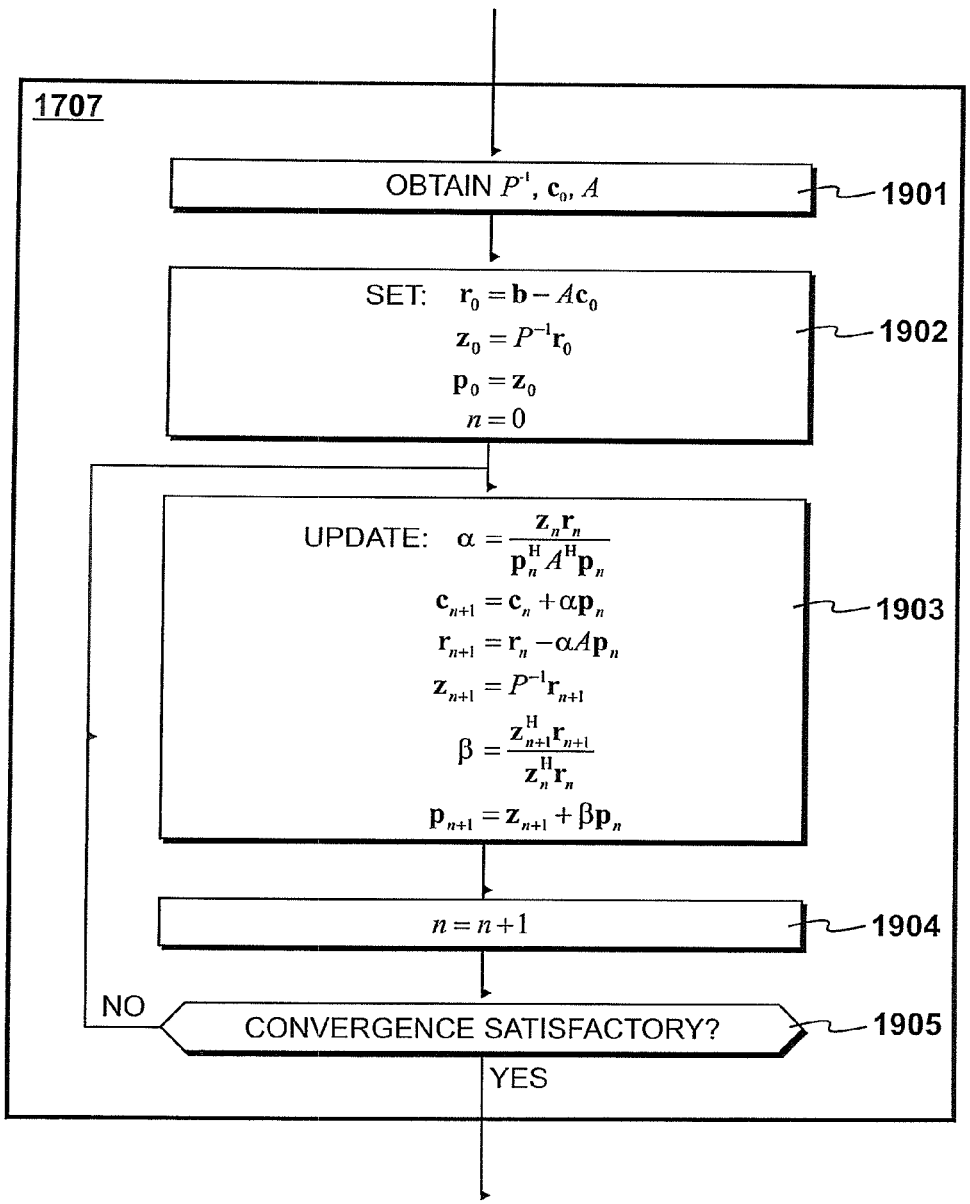
FIG. 19 details steps carried out during FIG. 17 to update an estimate of the image data.

FIG. 19 details step 1707, at which the next estimate $m_k$ of the image data is obtained using the conjugate gradients algorithm described with respect to FIG. 18.

At step 1901 the matrices $P^{-1}$ (matrix 1505), $c_0$ (the current estimate $m_k$ of the image data) and A (matrix 1406) are retrieved from memory and at step 1902 a number of variables are initialised as follows: $r_0$ is initialised to be the product of A and $c_0$ subtracted from b; $z_0$ is initialised to be the product of $P^{-1}$ and $r_0$, $p_0$ is initialised to be $z_0$, and a counter n is set to zero:

$r_0 = b - Ac_0$ $z_0 = P^{-1} r_0$ $p_0 = z_0$ n=0

At step 1903 the variables are updated as follows: a variable $\alpha$ is set to be the product of $z_n$ and $r_n$ divided by the product of the Hermitian transpose of $p_n$, the Hermitian transpose of A and $p_n$; $c_{n+1}$ is updated to the sum of c, and the product of and $p_n$; $r_{n+1}$ is updated to the product of $\alpha$, A and $p_n$ subtracted from $r_n$; a variable $\beta$ is set to be the product of the Hermitian transpose of $z_{n+1}$ and $r_{n+1}$ divided by the product of the Hermitian transpose of $z_n$ and $r_n$; and $p_{n+1}$, is updated to be sum of $z_{n+1}$ and the product of $\beta$ and $p_n$:

$$\alpha = \frac{z_n r_n}{p_n^H A^H p_n}$$

$$c_{n+1} = c_n + \alpha p_n$$

$$r_{n+1} = r_n - \alpha A p_n$$

$$z_{n+1} = P^{-1} r_{n+1}$$

$$\beta = \frac{z_{n+1}^H r_{n+1}}{z_n^H r_n}$$

$$p_{n+1} = z_{n+1} + \beta p_n$$

At step 1904 n is incremented by one, and at step 1905 a question is asked as to whether satisfactory convergence has been reached, indicated by the closeness of the calculated $r_{n+1}$ to zero. If it is not close enough, another iteration of step 1903 is carried out. Alternatively, convergence is satisfactory and step 1707 is complete. The last value of $c_{n+1}$ is used as the result and becomes the next estimate of $m_k$.

Other methods of implementing the Conjugate Gradients algorithm are available, but in all cases the pre-conditioner 1804 may be used to speed up the convergence.

FIG. 20

The description now turns to the way in which the estimate of the covariance of the noise $\Sigma_n$ is initialised and updated during steps 1705 and 1708 respectively.

As described with reference to FIG. 14, prior art methods of analysing ultrasound data assume that the noise 1303, n, is invariant across the scatterer field, but better results can be obtained by assuming that this is not the case. However, around a scatterer it is assumed that there exists some region where the noise is effectively constant. Thus, for example, in our image space 1001 there is a region 2001 around a scatterer 2002 in which the noise can be assumed to be substantially constant. Starting from equation 1310, that the time trace is equal to the product of the blurring matrix and the image data minus the noise, the noise can be written as the product of the blurring matrix and the image data subtracted from the time trace, as shown at 2003.

Thus the variance of the noise within region 2001 can be estimated using the sum of the squares of the residuals within that region, using the latest estimate $m_k$ of the image data. This can be done for a plurality of regions to obtain a result for the estimate of the covariance matrix $\Sigma_n$ at the kth iteration.

The procedure is simplified by assuming that $\Sigma_{n,k}$ is diagonal, meaning that only the diagonal elements need to be calculated. The element in the ith row and ith column is estimated as follows. A set of entries in the current estimate of the image data, $m_k$, is denoted $S_{sub,i}$. This corresponds to a region such as region 2001 of the image data. For each point in this region, the magnitude of the residual of the blurring matrix H multiplied by the current estimate $m_k$ of the image data, subtracted from the time trace y is squared. The result is divided by two and summed for all j in the set $S_{sub,i}$, and this sum is divided by the size of the set $S_{sub,i}$. This is given by equation 2004:

$$\left(\hat{\Sigma}_{n,k}\right)_{i,i} = \frac{1}{N_{S_{sub,i}}} \sum_{j \in S_{sub,i}} \frac{1}{2}\|(y - Hm_k)_j\|^2$$

Each entry in the diagonal matrix $\Sigma_{n,k}$ is calculated like this, giving the full estimate $\Sigma_{n,k}$ at step 1708. This estimate of the variance of the noise is made possible by assuming that the noise varies across the image data, but is locally invariant in any small enough region.

This equation is used to initialise the estimate of the variance of the noise using $m_0$, as well as to update it at each iteration.

This method of estimating the variance of the noise could be used with other versions of the Expectation Maximisation algorithm. In particular, it could be used with other methods for initialising and updating both the estimate of the mean of the distribution of the image data and the estimate of the echogenicity.

The echogenicity $S_k$ is initialised and updated at each iteration in any suitable way.

FIG. 21

The algorithm described herein with reference to FIGS. 13 to 20 estimates image data to be displayed on a display, given input data as a plurality of time traces and a blurring matrix. It can be used to provide less blurred images than those currently available using traditional ultrasound machines. However, it is also useful in that it can provide good quality ultrasound images using a relatively small amount of processing power memory.

Figure 21:
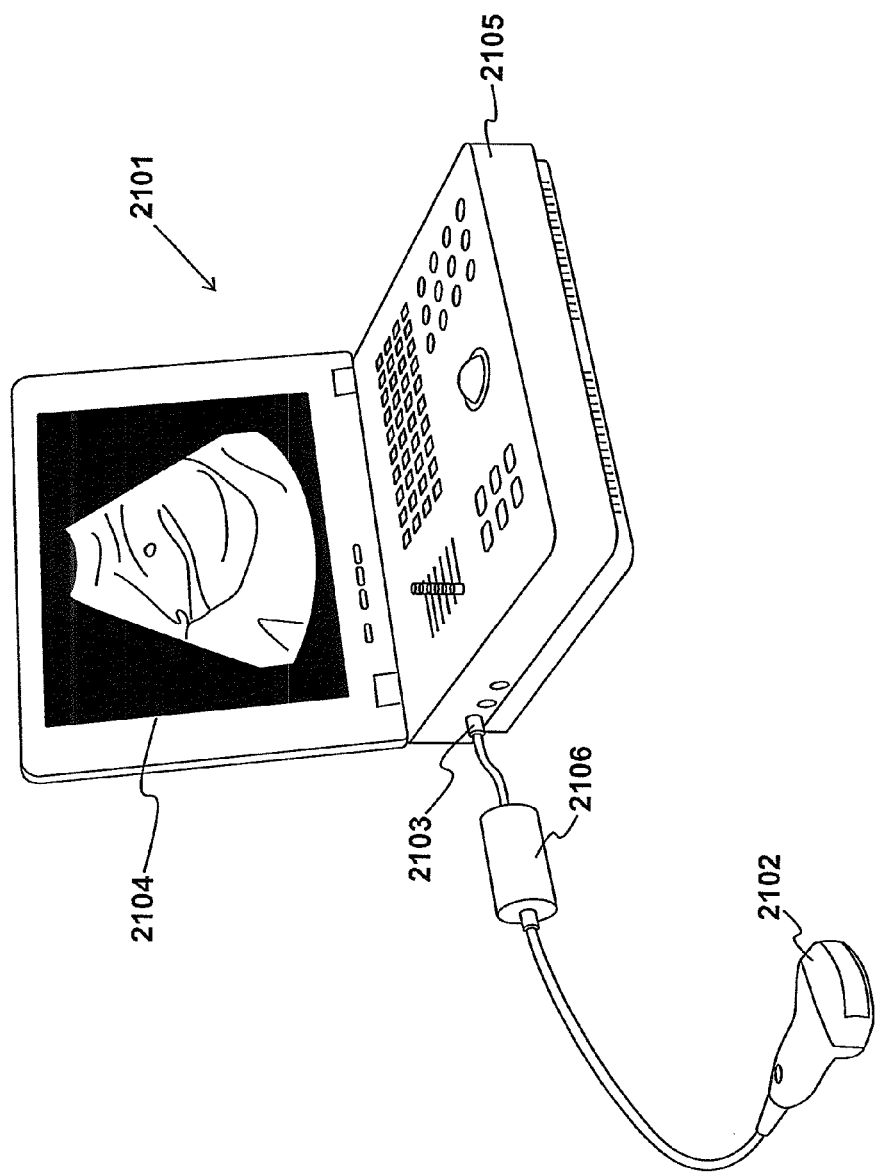
FIG. 21 illustrates an alternative ultrasound machine that may be used with the invention.

A portable ultrasound machine is illustrated in FIG. 21. Portable machine 2101 resembles a laptop computer, and has similar limitations in terms of the available processing power and memory. Typically, a probe 2102 plugs into a port 2103, such as a USB port, and the time traces it produces are displayed on display 2104. A keyboard interface 2105 is provided to allow control of the system by an operator.

In an embodiment of the invention, a device 2106 is placed between probe 2102 and port 2103. The USB device configures system 2101 to carry out the method described herein, rather than its normal method. Thus, a standard portable machine can be easily modified to produce improved image data. Other methods of introducing executable instructions into the processor of an ultrasound machine are also contemplated. Alternatively, newer ultrasound machines may as standard be built with these instructions embedded.

What is claimed is:

1. Apparatus for producing image data representing a specimen being imaged using ultrasound, comprising a processor and memory, wherein said processor is configured to:
   receive input data representing an output from an ultrasound probe;
   process said input data to produce output image data; and
   output said output image data;
   said processor being configured to carry out said step of processing said input data by:
   obtaining a first matrix that is dependent upon attributes of said probe and on the way in which said input data was produced;
   initialising estimates for the image data, echogenicity of said image data, and variance of noise of said image data;
   iteratively performing the following steps until a predetermined level of convergence is reached:
   (a) update said estimate of said image data using: said first matrix, a respective said estimate of said echogenicity, a respective said estimate of said variance of said noise, and said input data,
   (b) update said estimate of the echogenicity using said updated estimate of said image data, and
   (c) update said estimate of the variance of the noise using said updated estimate of said image data;
   wherein step (c) is performed using an update rule that assumes the noise to be varying across said image data but locally invariant for any small enough region of said image data; and
   using a converged estimate of said image data to produce said output image data.

2. Apparatus according to claim 1, wherein said update rule for step (c) is:

$$\left(\hat{\Sigma}_{n,k}\right)_{i,i} = \frac{1}{N_{S_{sub,i}}} \sum_{j \in S_{sub,i}} \frac{1}{2}\|(y - Hm_k)_j\|^2$$

where:
$(\hat{\Sigma}_{n,k})_{i,i}$ is an entry in the ith row and ith column of a matrix representing the estimate of the variance of the noise at a kth iteration;
H is said first matrix;
$m_k$ is the estimate of the image data at the kth iteration;

y is said input data;

$S_{sub,i}$ is a set of entries in $m_k$ corresponding to a region of said image data across which the noise is assumed to be invariant; and $N_{S_{sub,i}}$ is the size of $S_{sub,i}$.

3. Apparatus according to claim 1, wherein said processor is configured to initialise said estimate of the image data using said first matrix and said image data.

4. Apparatus according to claim 3, wherein said processor is further configured to obtain a constant and evaluate a second matrix using said first matrix and said constant, and is configured to initialise said estimate of the image data additionally using said second matrix.

5. Apparatus according to claim 4, wherein said processor is configured to initialise said estimate of said image data by calculating the product of:
(a) said second matrix,
(b) a transpose of said first matrix, and
(c) said image data.

6. Apparatus according to claim 4, wherein said second matrix is the inverse of the sum of:
(a) the product of: a transpose of the first matrix, and the first matrix, and
(b) the product of: said constant, and an identity matrix having the same dimensions as said first matrix.

7. Apparatus according to claim 4, wherein said constant represents noise-to-signal ratio of the image data.

8. Apparatus according to claim 4, wherein an algorithm used in step (a) is the Conjugate Gradients algorithm.

9. Apparatus according to claim 8, wherein each iteration of step (a) uses said second matrix as a preconditioner in the algorithm.

10. Apparatus according to claim 1, wherein said processor is configured to update the estimate of the echogenicity additionally using said input data.

11. A method of producing image data representing a specimen being imaged using ultrasound, comprising the steps of:
receiving input data representing an output from an ultrasound probe;
processing said input data to produce output image data; and
outputting said output image data to a display;
wherein said step of processing said input data comprises:
obtaining a first matrix that is dependent upon attributes of said probe and on the way in which said input data was produced;
initialising estimates for the image data, echogenicity of said image data, and variance of noise of said image data;
iteratively performing the following steps until a predetermined level of convergence is reached:
(a) update said estimate of said image data using: said first matrix, a respective said estimate of said echogenicity, a respective said estimate of said variance of said noise, and said input data,
(b) update said estimate of the echogenicity using said estimate of said image data, and
(c) update said estimate of the variance of the noise using said estimate of said image data;
wherein step (c) is performed using an update rule that assumes the noise to be varying across said image data but locally invariant for any small enough region of said image data; and using a converged estimate of said image data to produce said output image data.

12. A method according to claim 11, wherein said update rule for step (c) is:

$$\left(\hat{\Sigma}_{n,k}\right)_{i,i} = \frac{1}{N_{S_{sub,i}}} \sum_{j \in S_{sub,i}} \frac{1}{2}\|(y - Hm_k)_j\|^2$$

where:

$(\hat{\Sigma}_{n,k})_{i,i}$ is an entry in the ith row and ith column of a matrix representing the estimate of the variance of the noise at a kth iteration;

H is said first matrix;

$m_k$ is the estimate of the image data at the kth iteration;

y is said input data;

$S_{sub,i}$ is a set of entries in $m_k$ corresponding to a region of said image data across which the noise is assumed to be invariant; and $N_{S_{sub,i}}$ is the size of $S_{sub,i}$.

13. A method according to claim 11, wherein said step of initialising said estimate of the image data is carried out using said first matrix and said image data.

14. A method according to claim 13, further comprising the steps of obtaining a constant and evaluating a second matrix using said first matrix and said constant, wherein said step of initialising said estimate of the image data is carried out additionally using said second matrix.

15. A method according to claim 14, wherein said step of initialising said estimate of said image data is carried out by calculating the product of:
(a) said second matrix,
(b) a transpose of said first matrix, and
(c) said image data.

16. A method according to claim 14, wherein said second matrix is the inverse of the sum of:
(a) the product of a transpose of the first matrix, and the first matrix, and
(b) the product of said constant and an identity matrix having the same dimensions as said first matrix.

17. A method according to claim 14, wherein said constant represents noise-to-signal ratio of the image data.

18. A method according to claim 14, wherein an algorithm used in step (a) is the Conjugate Gradients algorithm.

19. A method according to claim 18, wherein each iteration of step (a) uses said second matrix as a preconditioner in the algorithm.

20. A non-transitory computer-readable medium encoded with program instructions executable by a computer that, when executed by a computer, cause a computer to perform steps of:
receiving input data representing an output from an ultrasound probe;
processing said input data to produce output image data; and
outputting said output image data to a display;
wherein said step of processing said input data comprises:
obtaining a first matrix that is dependent upon attributes of said probe and on the way in which said input data was produced;
initialising estimates for the image data, echogenicity of said image data, and variance of noise of said image data;
iteratively performing the following steps until a predetermined level of convergence is reached:
(a) update said estimate of said image data using: said first matrix, a respective said estimate of said echogenicity, a respective said estimate of said variance of said noise, and said input data, (b) update said estimate of the echogenicity using said estimate of said image data, and (c) update said estimate of the variance of the noise using said estimate of said image data;

wherein step (c) is performed using an update rule that assumes the noise to be varying across said image data but locally invariant for any small enough region of said image data; and using said converged estimate of said image data to produce said output image data.

* * * * *